United States Patent
Baba

(10) Patent No.: US 10,451,565 B2
(45) Date of Patent: Oct. 22, 2019

(54) X-RAY APPARATUS FOR MEASURING SUBSTANCE QUANTITY

(71) Applicant: BEAMSENSE Co., Ltd., Osaka (JP)

(72) Inventor: Sueki Baba, Osaka (JP)

(73) Assignee: BEAMSENSE Co., Ltd., Osaka (JP)

(*) Notice: Subject to any disclaimer, the term of this patent is extended or adjusted under 35 U.S.C. 154(b) by 277 days.

(21) Appl. No.: 15/518,566

(22) PCT Filed: Aug. 11, 2015

(86) PCT No.: PCT/JP2015/072772
§ 371 (c)(1),
(2) Date: May 2, 2017

(87) PCT Pub. No.: WO2016/059862
PCT Pub. Date: Apr. 21, 2016

(65) Prior Publication Data
US 2017/0284849 A1    Oct. 5, 2017

(30) Foreign Application Priority Data

Oct. 16, 2014    (JP) .................................. 2014-211976

(51) Int. Cl.
*G01N 23/04*    (2018.01)
*G01F 23/288*    (2006.01)

(52) U.S. Cl.
CPC ........... *G01N 23/04* (2013.01); *G01F 23/288* (2013.01); *G01N 2223/639* (2013.01)

(58) Field of Classification Search
CPC .................. G01F 23/288; G01N 23/04; G01N 2223/633; G01N 2223/635; G01N 2223/637; G01N 2223/639; G01N 2223/64
See application file for complete search history.

(56) References Cited

U.S. PATENT DOCUMENTS

| | | | |
|---|---|---|---|
| 6,201,850 B1 * | 3/2001 | Heumann | G01N 23/04 378/22 |
| 6,698,470 B1 * | 3/2004 | Horn | G01N 35/1079 73/863.01 |
| 2009/0010388 A1 * | 1/2009 | Stahly | G01N 21/253 378/79 |

FOREIGN PATENT DOCUMENTS

| | | |
|---|---|---|
| JP | H05322630 A | 12/1993 |
| JP | 2002357472 A | 12/2002 |
| JP | 2014059220 A | 4/2014 |

OTHER PUBLICATIONS

Translation of JP 2014-059220 A (Year: 2014).*
International Search Report dated Sep. 8, 2015 in corresponding Application No. PCT/JP2015/072772; 2 pgs.

(Continued)

*Primary Examiner* — Chih-Cheng Kao
(74) *Attorney, Agent, or Firm* — Maier & Maier, PLLC

(57) ABSTRACT

This X-ray apparatus for measuring a substance quantity includes: an X-ray irradiating unit for irradiating X-rays from above or below a container which contains a substance to be measured; an imaging unit which is disposed so as to face the X-ray irradiating unit with the container between the imaging unit and the X-ray irradiating unit, and which obtains image data on the basis of the transmitted X-rays passing through the container; and a substance quantity calculating unit which processes the obtained image data and calculates the quantity of the substance to be measured, on the basis of the intensity of the transmitted X-rays for each pixel in the container.

6 Claims, 3 Drawing Sheets

(56) References Cited

OTHER PUBLICATIONS

Translation of the International Preliminary Report on Patentability dated Apr. 27, 2017, in connection with corresponding International Application No. PCT/JP2015/072772 (6 pgs.).

* cited by examiner

X-RAY APPARATUS FOR MEASURING SUBSTANCE QUANTITY

TECHNICAL FIELD

The present invention relates to an X-ray apparatus for measuring a substance quantity for measuring the amount of a substance in a container by using X-rays. Particularly, the present invention relates to an X-ray apparatus for measuring substance quantity for measuring a minute amount of a substance in a container using X-rays, for example, a liquid volume of a minute amount of liquid.

BACKGROUND ART

Heretofore, there is known an apparatus for detecting the liquid level by using X-rays for measuring the liquid volume of a sealed container, as shown in Japanese Patent Laid-open Publications No. H05-322630 A and 2002-357472 A In the above conventional method, since X-rays are irradiated in a horizontal direction with respect to the liquid surface, it can be detected only in the case of a liquid having a constant liquid level in the entire container, and no consideration has been given to measuring the liquid volume of a minute amount of locally present liquid.

SUMMARY OF THE INVENTION

An object of the present invention is to provide an X-ray apparatus for measuring substance quantity for measuring the quantity of a minute amount of substance locally present in a container.

The X-ray apparatus for measuring substance quantity according to the present invention includes:

an X-ray irradiating unit for irradiating X-rays from above or below a container which contains a substance to be measured;

an imaging unit which is disposed so as to face the X-ray irradiating unit with the container between the imaging unit and the X-ray irradiating unit, and which obtains image data on the basis of the transmitted X-rays passing through the container; and a substance quantity calculating unit which processes the obtained image data and calculates the quantity of the substance to be measured, on the basis of the intensity of the transmitted X-rays for each pixel in the container.

According to the X-ray apparatus for measuring substance quantity according to the present invention, the amount of the substance to be measured is calculated based on the intensity of the transmitted X-rays for each pixel obtained by irradiating X rays from above or below the container, and it is possible to measure not only the liquid representing the liquid level over the entire container but also the minute amount of substances locally present.

DENOTATION OF REFERENCE NUMERALS

Figure 1:
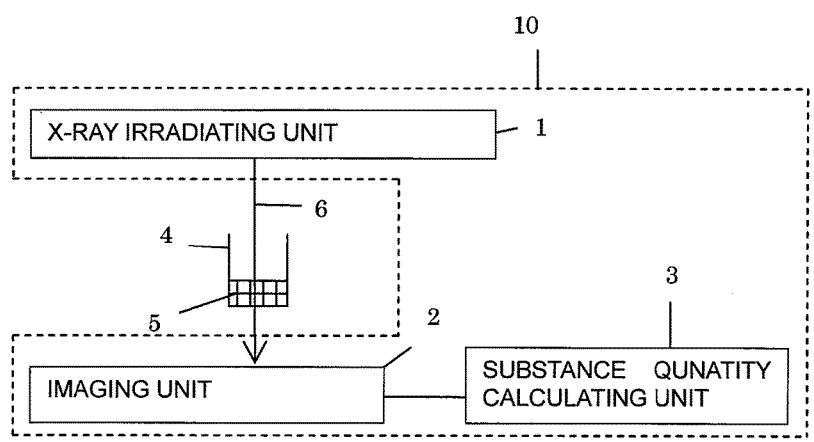
FIG. 1 is a block diagram showing a configuration of an X-ray apparatus for measuring substance quantity according to the embodiment 1.

1 X-ray irradiation unit
2 imaging unit
3 substance quantity calculation unit
4 container
5 liquid (substance to be measured)
6 X-ray
10 X-ray apparatus for measuring substance quantity
11 CPU
12 memory
13 storage device
14 input-output device
15 display device
16 interface
20 microplate

DETAILED DESCRIPTION

An X-ray apparatus for measuring substance quantity according to first aspect includes:

an X-ray irradiating unit for irradiating X-rays from above or below a container which contains a substance to be measured;

an imaging unit which is disposed so as to face the X-ray irradiating unit with the container between the imaging unit and the X-ray irradiating unit, and which obtains image data on the basis of the transmitted X-rays passing through the container; and a substance quantity calculating unit which processes the obtained image data and calculates the quality of the substance to be measured, on the basis of the intensity of transmitted X-rays for each pixel in the container.

In the X-ray apparatus for measuring substance quantity according to second aspect, the substance quantity calculating unit may calculate the quantity of substance to be measured in the container based on the integrated intensity of the transmitted X-rays over all the pixels in the container according to the first aspect.

In the X-ray apparatus for measuring substance quantity according to third aspect, the substance quantity calculating unit may calculate the height of the substance to be measured for each of the pixels on the basis of the intensity of the transmitted X-rays for each pixel in the container according to the first aspect or second aspect.

In the X-ray apparatus for measuring substance quantity according to fourth aspect, the substance quantity calculating unit may calculate the quantity of substance to be measured on the basis of a calibration curve showing the relationship with based on the quantity of substance obtained from the intensity of the transmitted X-rays by the plurality of quantified substances to be measured and the intensity of the transmitted X-rays according to any one of the first to third aspects.

In the X-ray apparatus for measuring substance quantity according to fifth aspect, the X-ray irradiating unit may irradiate X-rays from above or below a container whose upper surface is hermetically sealed according to any one of the first to fourth aspects.

In the X-ray apparatus for measuring substance quantity according to sixth aspect, the X-ray irradiation unit may irradiate X-rays from above or below a microplate in which a plurality of containers are two-dimensionally arranged according to any one of the first to fifth aspects.

In the X-ray apparatus for measuring substance quantity according to seventh aspect, the imaging unit may be an area sensor according to any one of the first to sixth aspects.

Hereinafter with reference to the drawings, the X-ray apparatus for measuring substance quantity according to an embodiment of the present invention will be described in detail. In the drawings, substantially the same members are denoted by the same reference numerals.

Embodiment 1

FIG. 1 is a block diagram showing a configuration of the X-ray apparatus for measuring substance quantity 10 according to the embodiment 1. This X-ray apparatus for measuring a substance quantity 10 includes: an X-ray irradiating unit 1 for irradiating X-rays 6 from above or below a container which contains a substance to be measured (target substance); an imaging unit 2 which is disposed so as to face the X-ray irradiating unit 1 with the container between the imaging unit and the X-ray irradiating unit, and which obtains image data on the basis of the transmitted X-rays passing through the container 4; and a substance quantity calculating unit 3 which processes the obtained image data and calculates the amount of liquid as the substance to be measured, on the basis of the intensity of the transmitted X-rays for each pixel in the container 4.

According to the X-ray apparatus for measuring substance quantity 10, the amount of liquid as the substance to be measured is calculated based on the intensity of transmitted X-rays for each pixel obtained by irradiating X-rays from above or below the container 4. Therefore, not only the liquid representing the liquid level over the entire container 4 but also the minute amount of substances present locally can be measured.

Each constituent member constituting the X-ray apparatus for measuring substance quantity 10 will be described below.

<X-Ray Irradiating Unit>

Any means may be used as the X-ray irradiating unit 1 as long as it can irradiate the container with X-rays 6, for example, an X-ray tube, a rotating anode X-ray tube, a beam line in a synchrotron radiation facility, or the like. Further, the X-rays 6 irradiated by the X-ray irradiation unit 1 may be any of characteristic X-rays, continuous X-rays, monochromatic optical X-rays, and the like.

The X-ray irradiation unit 1 irradiates X-rays from above or below the container 4 containing the substance to be measured 5 (that is, in a vertical direction).

<Substance to be Measured (Target Substance)>

Here, the substance to be measured may be any substance as long as it is a homogeneous substance, and may be any of a liquid, a powder and granular material, a small solid, and the like. Incidentally, in the case of a liquid or a powder and granular material, a container is required, but in the case of a small solid, a container is not required.

<Container>

As the container 4 for irradiating the X-ray 6 with the X-ray irradiation unit 1, for example, a container whose upper surface is hermetically sealed may be used. In this case, the upper surface may be hermetically sealed with a film which does not transmit visible light.

Figure 4:
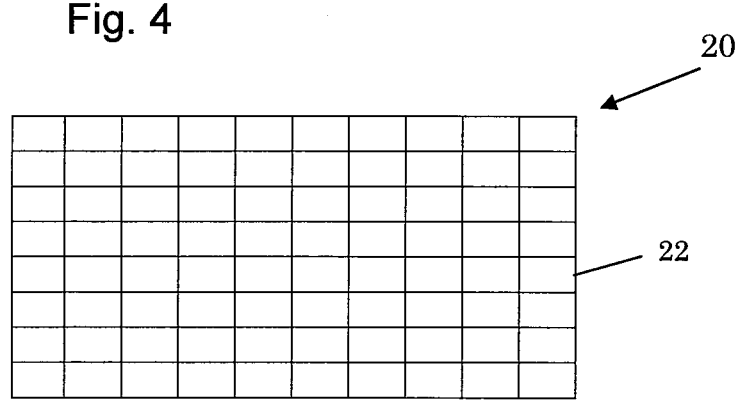
FIG. 4 is a plan view of a microplate in which a plurality of containers are two-dimensionally arranged.

FIG. 4 is a plan view of the microplate 20 in which a plurality of containers 22 are two-dimensionally arranged. As the container, a microplate 20 in which a plurality of containers 22 are two-dimensionally arranged as shown in FIG. 4 may be used.

In the case of the above-described conventional technique, it was impossible to measure the liquid amount of each container (pallet) 22 such as the microplate 20 in which the plurality of containers 22 are two-dimensionally arranged, even if it is effective for a single container. In contrast, according to the X-ray apparatus for measuring substance quantity 10 according to the embodiment 1, even in the case of the microplate 20 in which the plurality of containers 22 are two-dimensionally arranged, the quantity of substance to be measured in each container (pallet) 22 can be measured, because the X-rays are irradiated from above or below the microplate 20.

<Imaging Unit>

The imaging unit 2 may be any as long as it can receive transmitted X-rays and can obtain image data based on the intensity of transmitted X-rays for each pixel.

For example, a CCD, a CMOS sensor, a flat panel X-ray image sensor, or the like may be used as the imaging unit 2. Further, the imaging unit 2 is not limited to an area sensor such as a surface state sensor which can obtain the two-dimensional image data as it is, but may be a line sensor. In the case of a line sensor, two-dimensional image data can be obtained by performing scanning in a direction intersecting the extending direction of the line sensor. Alternatively, the imaging unit may be a point sensor.

<Substance Quantity Calculating Unit>

The substance quantity calculating unit 3 processes the image data and calculates the quantity of the substance to be measured in the container based on the intensity of the transmitted X-rays for each pixel in the containers 4 and 22. The substance quantity calculating unit 3 may be realized by, for example, an electric circuit or a semiconductor circuit, or may be realized as the substance quantity calculating unit 3 by software operating on a computer.

Figure 2:
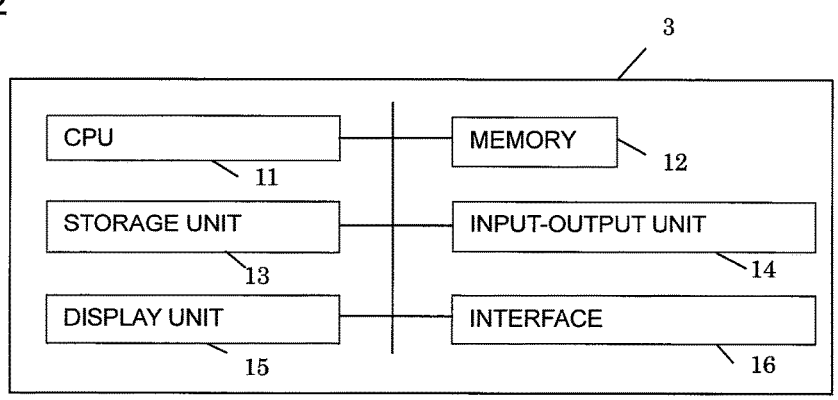
FIG. 2 is a block diagram showing a physical configuration in a case where the substance quantity calculating unit of the X-ray apparatus for measuring substance quantity is realized by a computer.

FIG. 2 is a block diagram showing a physical configuration when the substance quantity calculating unit 3 is realized by a computer. As shown in FIG. 2, as long as the computer has a general physical configuration, it suffices that the computer includes the CPU 11, the memory 12, the storage unit 13, the input-output unit 14, the display unit 15, and the interface 16.

The substance quantity calculating unit 3 may calculate the amount of the substance to be measured in the container based on the integrated intensity of the transmitted X-rays over all the pixels in the container. Alternatively, the height of the substance to be measured for each pixel may be calculated based on the intensity of transmitted X-rays for each pixel in the container but the height is the liquid surface (liquid amount), in the case of a liquid.

Figure 3:
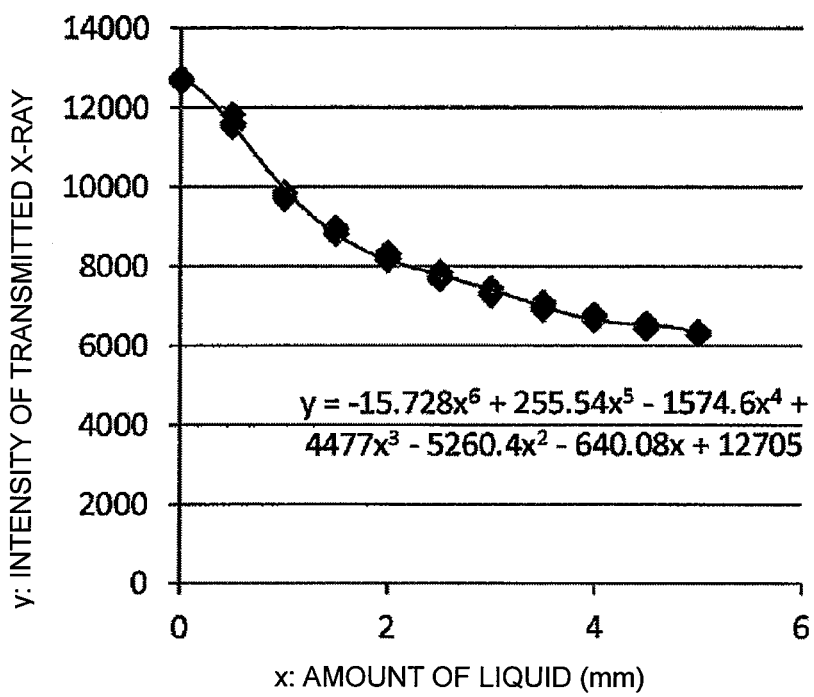
FIG. 3 is a graph showing a calibration curve showing a relationship between a amount of a liquid and a strength of transmitted X-rays when the substance to be measured is a liquid.

FIG. 3 is a graph showing a calibration curve showing the relationship between the liquid amount and the intensity of transmitted X-rays when the substance to be measured is a liquid. As the amount of the liquid which X-rays pass through increases, the intensity of the transmitted X-rays decreases. In addition, the decreasing curve of the transmitted X-rays may be represented by a linear interpolation curve so that the data points are passed through, for example, as shown in FIG. 3. Alternatively, it may be represented by a linear approximation curve using each data point. Further, it may be approximated by a nonlinear curve or the like using an exponential function or the like.

By using the calibration curve showing the relationship between the amount of the liquid and the intensity of the transmitted X-ray shown in FIG. 3, it is possible to calculate the liquid amount of the liquid to be measured from the intensity of the transmitted X-rays. In this case, by setting the intensity of transmitted X-rays in the calibration curve to the intensity of each pixel, the liquid volume can be calculated for each pixel as it is. Alternatively, it is also possible to calculate the average liquid volume in the container from the integrated intensity over all the pixels in the container. Based on the calibration curve showing the relationship between the amount of the liquid obtained from the intensity of the transmitted X-rays by the plurality of quantified liquids and the intensity of the transmitted X-rays, the substance quantity calculating unit 3 may calculate the liquid volume in the container.

Example

Figure 5A:
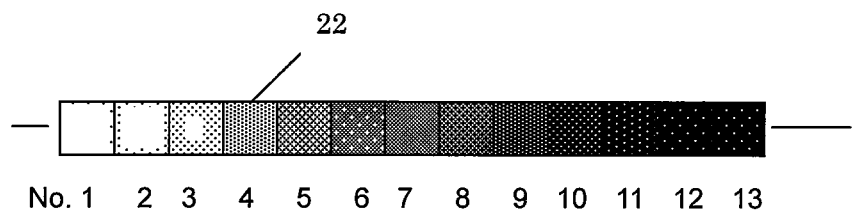
FIG. 5A is a plan view showing a state in which a liquid is used as a substance to be measured in a plurality of containers arranged one-dimensionally in Example 1, and the liquid volume of each container is different.
Figure 5B:
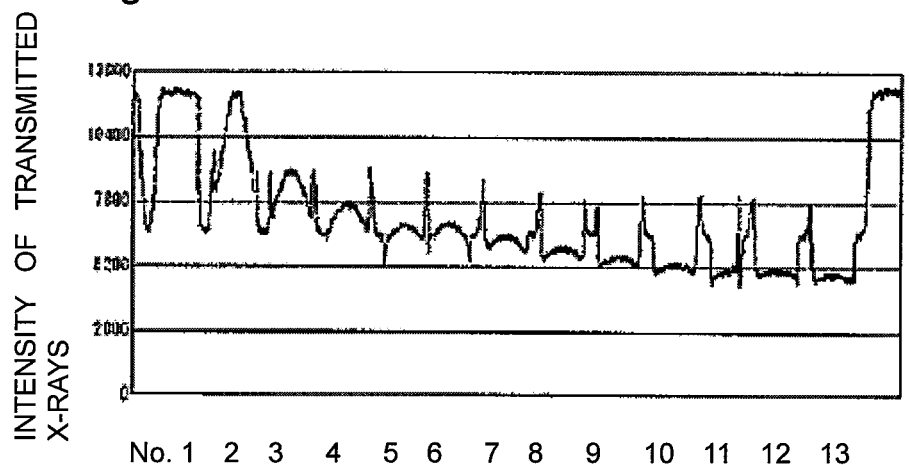
FIG. 5B is an intensity profile of transmitted X-rays when X-rays are irradiated along a line of a plurality of containers arranged one-dimensionally in FIG. 5 (a).

FIG. 5A is a plan view showing a state in which liquid is used as a substance to be measured in a plurality of containers 22 one-dimensionally arranged in Example 1, and liquid volumes of respective containers are different, and FIG. 5B is an intensity profile of transmitted X-rays when X-rays are irradiated along a line of a plurality of containers 22 one-dimensionally arranged in FIG. 5A.

In this example, thirteen containers from the container 1 to the container 13 are arranged one-dimensionally. According to the intensity profile of transmitted X-rays when X-rays are irradiated along a line as shown in FIG. 5B, in the case of having a substantially uniform liquid level, approximately the same transmitted X-ray intensity is shown throughout the containers 22 from the container 4 to the container 13.

On the other hand, when liquid locally exists around the container as containers 1 to 3, the transmitted X-ray intensity decreases only in the periphery. It is to be noted that, in this example, the case where the liquid remains around the periphery, that is, the case where the contact angle is an acute angle due to the surface tension and the liquid exists along the wall of the container is shown, but the present invention is not limited thereto. For example, the contact angle may be an obtuse angle.

Figure 6:
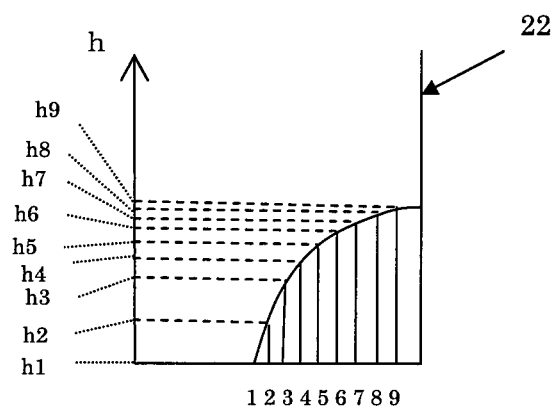
FIG. 6 is a schematic view showing a relationship between each position and a corresponding liquid height when a liquid locally exists in one container.

FIG. 6 is a schematic diagram showing the relationship between each position 1 to 9 and corresponding liquid height h 1 to h 9 in the case where a liquid locally exists in one container 22.

The transmitted X-rays in each pixel corresponding to each position 1 to 9 shows the intensity corresponding to the liquid amount h 1 to h 9 at each position 1 to 9. Therefore, the liquid amount (height) for each pixel can be calculated based on the intensity of the transmitted X-ray in each pixel corresponding to each position 1 to 9.

The X-ray apparatus for measuring substance quantity according to the present invention calculates the quantity of a substance to be measured based on the intensity of transmitted X-rays for each pixel obtained by irradiating X-rays from above or below the container. Therefore, in the case of a liquid as a substance to be measured, it can be used as a device for measuring not only a liquid representing the liquid level over the entire container but also the liquid amount with respect to a minute amount of liquid locally present.

The invention claimed is:

1. An X-ray apparatus for measuring a substance quantity comprising:
    an X-ray irradiating unit for irradiating X-rays from above or below a container which contains a substance to be measured;
    an imaging unit which is disposed so as to face the X-ray irradiating unit with the container between the imaging unit and the X-ray irradiating unit, and which obtains image data on the basis of the transmitted X-rays passing through the container;
    a substance quantity calculating unit which processes the obtained image data and calculates the quantity of the substance to be measured, on the basis of the intensity of the transmitted X-rays for each pixel in the container; and
    wherein the substance quantity calculating unit calculates the height of the substance to be measured for each pixel based on the intensity of the transmitted X-ray for each pixel in the container.

2. The X-ray apparatus for measuring substance quantity according to claim 1, wherein the substance quantity calculating unit calculates the quantity of the substance in the container based on integrated intensity of transmitted X-rays over all pixels in the container.

3. The X-ray apparatus for measuring substance quantity according to claim 1, wherein the substance quantity calculating unit calculates the quantity of the substance based on a calibration curve showing a relationship between the quantity of substance obtained from the intensity of transmitted X-rays by a plurality of quantified measured substances and the intensity of the transmitted X-ray.

4. The X-ray apparatus for measuring substance quantity according to claim 1, wherein the X-ray irradiating unit irradiates X-rays from above or below the container whose upper surface is hermetically sealed.

5. The X-ray apparatus for measuring substance quantity according to claim 1, wherein the X-ray irradiating unit irradiates X-rays from above or below a microplate in which a plurality of containers are two-dimensionally arranged.

6. The X-ray apparatus for measuring substance quantity according to claim 1, wherein the imaging unit is an area sensor.

* * * * *